(12) United States Patent
Watanabe et al.

(10) Patent No.: US 10,022,103 B2
(45) Date of Patent: Jul. 17, 2018

(54) X-RAY DIAGNOSTIC APPARATUS

(71) Applicant: Toshiba Medical Systems Corporation, Otawara-shi (JP)

(72) Inventors: Yuichiro Watanabe, Yaita (JP); Naoki Uchida, Utsunomiya (JP); Ryoichi Nagae, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 122 days.

(21) Appl. No.: 15/079,676

(22) Filed: Mar. 24, 2016

(65) Prior Publication Data

US 2016/0287199 A1    Oct. 6, 2016

(30) Foreign Application Priority Data

Mar. 30, 2015  (JP) .................................. 2015-070380
Nov. 17, 2015  (JP) .................................. 2015-224823

(51) Int. Cl.
*A61B 6/00*    (2006.01)

(52) U.S. Cl.
CPC .............. *A61B 6/542* (2013.01); *A61B 6/465* (2013.01); *A61B 6/4441* (2013.01)

(58) Field of Classification Search
None
See application file for complete search history.

(56) References Cited

U.S. PATENT DOCUMENTS 9,655,585 B2 *  5/2017  Watanabe .............. A61B 6/542
2015/0139393 A1  5/2015  Watanabe et al.

FOREIGN PATENT DOCUMENTS

JP          2012-55510          3/2012

OTHER PUBLICATIONS

GE Healthcare "Dose Map: Visualize the estimated cumulated local patient dose all along the exam," http://www.youtube.com/watch?y=c_NatruhieY, May 13, 2013, 2 Pages.

\* cited by examiner

*Primary Examiner* — Hoon Song
(74) *Attorney, Agent, or Firm* — Oblon, McClelland, Maier & Neustadt, L.L.P.

(57) ABSTRACT

An X-ray diagnostic apparatus according to an embodiment includes an X-ray generator, processing circuitry, and a display unit. The X-ray generator radiates an X-ray. The processing circuitry obtains an exposure dose of a subject due to the X-ray radiated from the X-ray generator and generates an image in which a dose distribution based on the exposure dose is superimposed on a three-dimensional model representing the subject. The display unit displays the image. The processing circuitry generates an image in which the dose distribution on a body surface on a rear side when observed in a first view direction, serving as a direction in which the three-dimensional model is displayed, is visible.

13 Claims, 7 Drawing Sheets

X-RAY DIAGNOSTIC APPARATUS

CROSS-REFERENCE TO RELATED APPLICATIONS

This application is based upon and claims the benefit of priority from Japanese Patent Application No. 2015-070380, filed on Mar. 30, 2015; and Japanese Patent Application No. 2015-224823, filed on Nov. 17, 2015, the entire contents of all of which are incorporated herein by reference.

FIELD

Embodiments described herein relate generally to an X-ray diagnostic apparatus.

BACKGROUND

An X-ray diagnostic apparatus irradiates a subject with an X-ray and detects the X-ray that has passed through the subject to display as an X-ray image, through which conditions of organs or blood vessels inside a body or the like can be perceived. However, in a case where the subject is irradiated with an excessive dose of X-rays, there is a risk that an inflammation or the like is caused in a skin. Therefore, it is required to control an exposure dose of the subject.

In order to control the exposure dose, some conventional X-ray diagnostic apparatuses are provided with a means with which a dose distribution is expressed by different colors to be displayed on a surface of a human body model representing the subject such that an operator can visually determine the dose distribution. When the dose distribution is displayed, the human body model is fixed to one direction such as a ventral surface, a back surface, or a side surface of the subject.

In the conventional X-ray diagnostic apparatus, however, the human body model displayed in a direction in which the dose distribution of a desired site is visible is sometimes different from an actual condition of the subject observed by the operator. In this case, a position of an X-ray generator or an arm relative to the subject is difficult to recognize. Therefore, it is not easy to determine an irradiation range of the X-ray.

DETAILED DESCRIPTION

An X-ray diagnostic apparatus includes an X-ray generator, processing circuitry and a display. The X-ray generator is configured to radiate an X-ray. The processing circuitry is configured to obtain an exposure dose of a subject due to the X-ray radiated from the X-ray generator and to generate an image in which a dose distribution based on the exposure dose is superimposed on a three-dimensional model representing the subject. The display is configured to display the image. The processing circuitry generates an image in which the dose distribution on a body surface on a rear side when observed in a first view direction, serving as a direction in which the three-dimensional model is displayed, is visible.

An X-ray diagnostic apparatus according to an embodiment is explained below with reference to the attached drawings.

First Embodiment

In an X-ray diagnostic apparatus 1 according to a first embodiment, a dose determination unit 20 obtains an exposure dose of a subject P and, based on this exposure dose, an image processor 15 generates an image of a dose distribution. Additionally, by making a human body model 141 representing the subject P transparent, the image processor 15 makes it possible to observe, by looking therethrough, the image of the dose distribution on a surface of the human body model 141, which image is not visible in a view direction serving as a current display direction of the human body model.

Hereinafter, respective members included in the X-ray diagnostic apparatus 1 according to the first embodiment will be described. Thereafter, display of the human body model and the image of the dose distribution will be described in detail.

Figure 1:
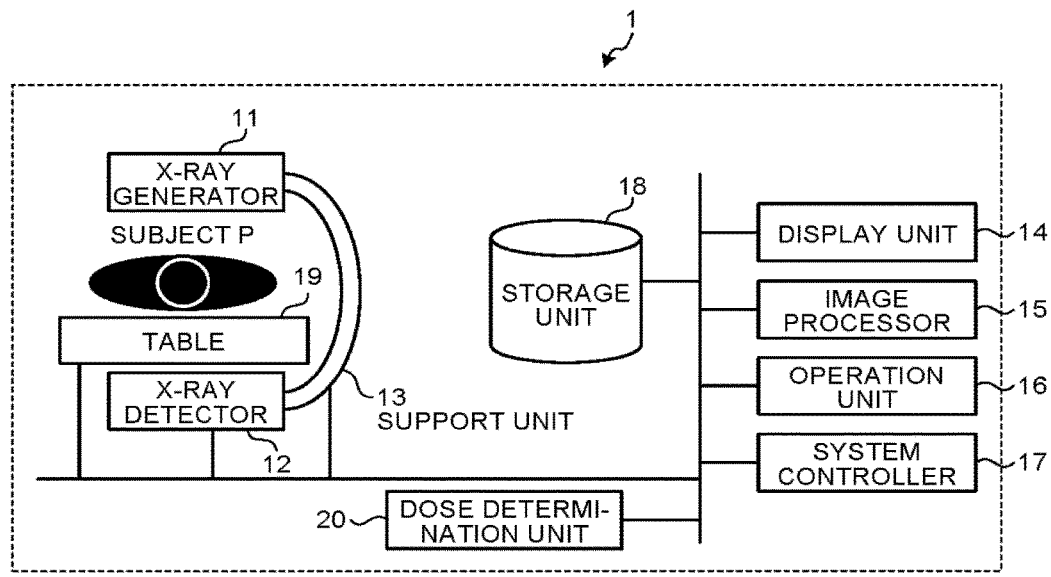
FIG. 1 is a diagram illustrating a configuration of an X-ray diagnostic apparatus according to a first embodiment.

FIG. 1 depicts a configuration of the X-ray diagnostic apparatus 1 according to the first embodiment. The X-ray diagnostic apparatus 1 includes an X-ray generator 11, an X-ray detector 12, a supporter 13, a display unit 14, the image processor 15, an operation unit 16, a system controller 17, a storage unit 18, a table 19, and the dose determination unit 20.

The X-ray generator 11 includes an X-ray tube, a collimator blade, a compensation filter, and a radiation quality adjustment filter. The X-ray tube is a vacuum tube and generates an X-ray upon being supplied with a high voltage. The collimator blade is a plate-shaped member made of lead or the like and provided in the vicinity of an X-ray irradiation port of the X-ray tube to adjust an irradiation range of the X-ray. The compensation filter is made of silicone rubber or the like and attenuates a predetermined X-ray component to avoid halation. The radiation quality adjustment filter is made of copper or aluminum, for example, and alters the radiation quality of the X-ray depending on a material or a thickness thereof. For example, the radiation quality adjustment filter reduces a soft radiation component which is easily absorbed by the subject P, or reduces a high energy component which is likely to cause deterioration of contrast in an X-ray image.

The X-ray detector 12 is an X-ray detection device including a photodiode or an image sensor, which detects an X-ray radiating from the X-ray generator 11 and attenuated by passing through the subject P.

Figure 2:
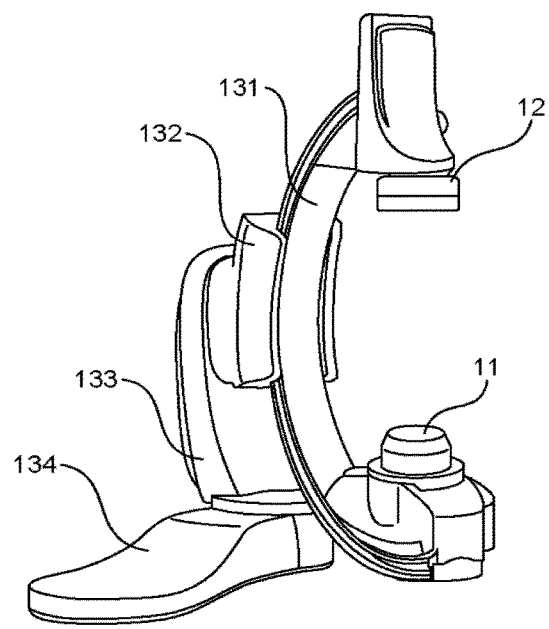
FIG. 2 is a view illustrating a supporter of the X-ray diagnostic apparatus according to the first embodiment.

The supporter 13 is a metal member that supports the X-ray generator 11 and the X-ray detector 12 such that both of the members oppose each other. Specifically, the supporter 13 includes, as illustrated in FIG. 2, an arm 131, an arm supporter 133, an arm connector 132 connecting the arm 131 and the arm supporter 133, and an arm base 134 fixing the arm supporter 133 on a floor surface. The arm 131 is slidable at the arm connector 132 in a direction along a shape of the arm 131. The arm connector 132 is rotatable at a connection point with the arm supporter 133 about an axis extending substantially in a horizontal direction. The arm supporter 133 is rotatable at a connection point with the arm base 134 about an axis extending substantially in a vertical direction. The supporter 13 slides or rotates as described above in accordance with input by an operator through the operation unit 16. As a result, an X-ray irradiation direction can be changed. A C-shaped arm has been described in FIG. 2 as an example. However, the arm may be an Ω-shaped arm.

Based on an X-ray irradiation condition or a geometric condition, the dose determination unit 20 obtains the exposure dose of the subject P.

The X-ray irradiation condition is determined by values such as setting values of a tube electric current and a tube voltage supplied to the X-ray tube of the X-ray generator 11, a setting value of the opening degree of collimator blade (a position of the blade), an attenuation amount of a predetermined component by the compensation filter or the radiation quality adjustment filter, and an irradiation time of the X-ray. A value of a dose area product meter may be employed as the X-ray irradiation condition. The dose area product meter is an apparatus that is provided in the vicinity of the X-ray tube and measures the radiated X-ray.

The geometric condition relates to rotation angles of the arm connector 132 and the arm supporter 133 of the supporter 13, and a positional relationship between the subject P and the X-ray generator 11 or a positional relationship between the X-ray generator 11 and the X-ray detector 12, which are determined based on a sliding distance of the arm 131 relative to the arm connector 132, or the like. In addition, the geometric condition may include a height of the table 19 on which the subject P is placed. The geometric condition may also include a rotation angle of a bed, where a rotation axis is parallel to a longitudinal direction thereof or perpendicular to the longitudinal direction thereof.

The image processor 15 generates an X-ray image based on the X-ray detected by the X-ray detector 12. The image processor 15 also adjusts the image quality such as contrast and brightness on this X-ray image. Additionally, the image processor 15 expresses the exposure dose of the subject P obtained by the dose determination unit 20 using different colors or brightness to generate as an image of the dose distribution. The image processor 15 then superimposes the image of the dose distribution on the human body model 141 representing the subject P to generate a display image displayed on the display unit 14. A plurality of patterns is prepared for the human body model 141 in advance based on a gender, a somatotype, a weight, and the like, such that an operator can select one in accordance with the subject P.

The image processor 15 can generate an image in which, by making the human body model 141 transparent, an invisible portion hidden on the surface of the human body model can be observed by being looked therethrough. For example, volume rendering processing is employed as the image generation processing.

Figure 3:
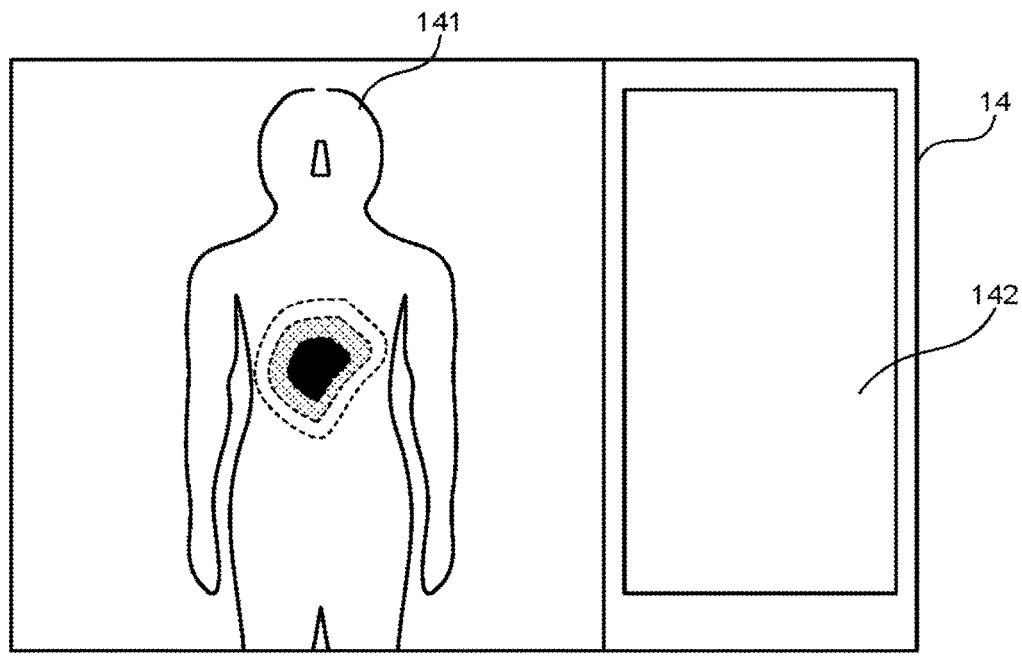
FIG. 3 is a diagram illustrating an example in which a dose distribution is displayed on a display unit according to the first embodiment by making a human body model transparent.

In order to describe the processing for making the human body model 141 transparent, FIG. 3 depicts an exemplary image in which a direction facing the subject P is taken as the view direction, and the dose distribution around a back of the subject P is displayed on the display unit 14 by making the human body model 141 transparent. Here, the view direction is a direction in which the human body model 141 is displayed on the display unit 14.

Figure 4:
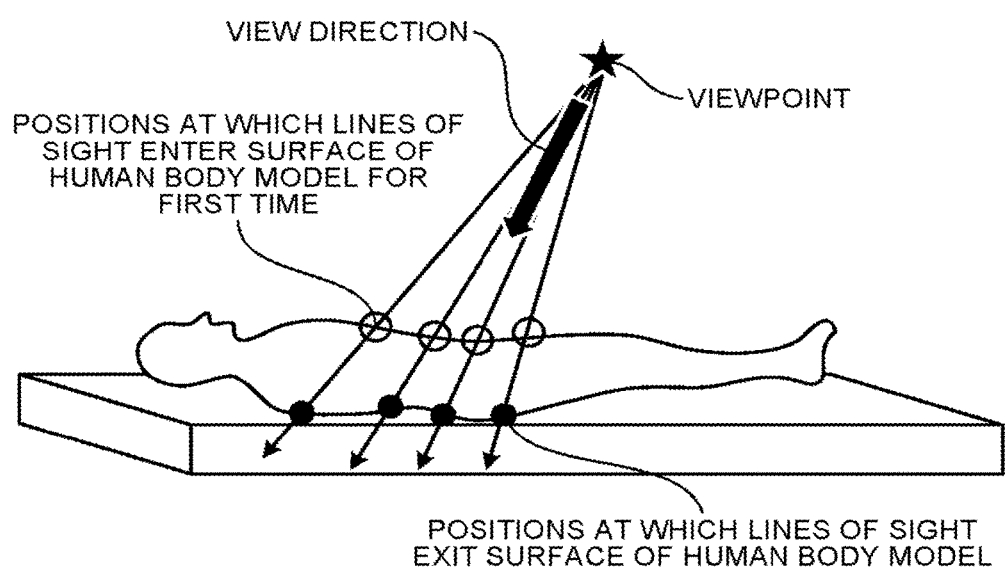
FIG. 4 is a diagram illustrating an exemplary positional relationship between a portion of the configuration of the X-ray diagnostic apparatus according to the first embodiment and a subject.

First, when observed in the view direction, which region is in a visible range on the surface of the human body model 141 or which region is an invisible region hidden on the surface of the human body model 141 is determined. For example, placing a viewpoint as illustrated in FIG. 4 is considered. On the surface of the human body model 141, when lines of sight (rendering paths) radially extend from a base point, namely, a viewpoint at which the view direction functions as the irradiation direction, positions at which the lines of sight enter the surface of the human body model 141 for the first time (outline circle marks in FIG. 4) are in a visible range in the view direction. On the other hand, on the surface of the human body model 141, positions at which the lines of sight exit the surface of the human body model 141 (black solid circle marks in FIG. 4) are in an invisible range in the view direction. In addition, positions at which the lines of sight enter the surface of the human body model 141 for the second time or thereafter are hidden by other portions of the human body model 141 and thus in the invisible range in the view direction. In the above description, whether to be visible or invisible in the view direction has been determined by radially extending the lines of sight from the viewpoint. However, the determination method is not limited thereto. For example, it is possible to determine whether to be visible or invisible in the view direction by making an infinite number of lines of sight parallel to the view direction enter the human body model 141.

When the invisible portion hidden on the surface of the human body model 141 is observed by being looked therethrough, the image processor 15 enhances the transparency of the image of the dose distribution on the surface of the human body model 141 within the visible range in the view direction. It is preferable that the human body model 141 be set to transparency in the volume rendering processing set to a level in which a shape thereof can be recognized (semi-transparency). The human body model 141 in an initial condition may be an image with no transparency, or alternatively, an image with some transparency. Upon displaying the invisible range in the view direction, the transparency thereof may be made higher. The visible range and the invisible range in the view direction may be differentiated by the transparency in the image of the dose distribution, making it possible to determine which of the ranges is the visible range in the view direction. A method for generating the image of the dose distribution by the image processor 15 may be changed between the visible range and the invisible range in the view direction. For example, in the visible range in the view direction, the image of the dose distribution is generated regardless of the degree of the exposure dose, whereas in the invisible range in the view direction, a threshold is set for the exposure dose and the image of the dose distribution is generated for the exposure dose equal to or higher than the threshold.

The storage unit 18 is a storage circuit including a hard disk, a semiconductor memory, or the like and stores data relating to the X-ray irradiation condition or the geometric condition for the X-ray generator 11, the X-ray detector 12, or the supporter 13. The storage unit 18 also stores the X-ray image generated based on the X-ray detected by the X-ray detector 12 or an image processed from the X-ray image by the image processor 15. Additionally, the storage unit 18 stores a program for the system controller 17 to execute and can store other information required for examination.

The display unit 14 includes a liquid crystal display, a light emitting diode (LED) display, or the like and displays the X-ray image generated based on the X-ray detected by the X-ray detector 12 or an image processed from that X-ray image by the image processor 15. In the display unit 14, an information display region 142 may be provided in addition to the human body model 141. The information display region 142 is a region that displays various types of information during examination and can display patient information, X-ray information, and other information as appropriate. The information display region 142 may also display a message display area that displays a warning, an operation guide, and the like.

The table 19 provided on the top of the bed is a plate-shaped member on which the subject P is placed. In addition, the table 19 can be moved in the longitudinal direction of the bed (a body axis direction of the subject P). Furthermore, for the purpose of tilting the subject P, the table 19 may be rotatable about a rotation axis, specifically, an axis parallel to the longitudinal direction of the bed or an axis perpendicular to the longitudinal direction of the bed.

The operation unit 16 includes an input device such as a touch panel, a mouse, a keyboard, or a joystick. The operation unit 16 may include a device capable of speech recognition, line-of-sight detection, or gesture recognition. Additionally, the operation unit 16 may be configured such that operation can be selected or operation content can be changed using a foot pedal.

Operation instructions such as rotation or opening/closing of the compensation filter, change of the radiation quality adjustment filter, change of the irradiation range of the X-ray through adjustment of the opening degree of collimator blade (a position of the blade), switching of the size of a visual field of the X-ray detector 12, switching of whether to save the captured X-ray image, and movement or rotation of the table 19 are input to the operation unit 16.

The system controller 17 reads the program stored in the storage unit 18 to execute and comprehensively controls the respective members constituting the X-ray diagnostic apparatus 1. For example, based on input information from the operator received by the operation unit 16, the system controller 17 sets the X-ray irradiation condition for the X-ray generator 11 or drives the supporter 13 to set the geometric condition for the supporter 13. In addition, the system controller 17 is capable of controlling a driving unit that manages movement or rotation of the bed.

The image processor 15, the system controller 17, and the dose determination unit 20 described above are processors. For example, these members are configured by circuits such as a dedicated or general central processing unit (CPU) or graphics processing unit (GPU), an application specific integrated circuit (ASIC), and a programmable logic device (for example, a simple programmable logic device (SPLD), a complex programmable logic device (CPLD), and a field programmable gate array (FPGA)).

The processor reads and executes a program stored in the storage unit 18 or directly built in the circuit of the processor to realize the function thereof. A memory for storing a program may be individually provided for each processor, or alternatively, a storage circuit of the storage unit 18 may store a program corresponding to the function of the processor. Each of the processors according to the embodiment is not limited to one that is configured as a single circuit for each processor. Alternatively, a plurality of separate circuits may be combined to configure one processor, thereby realizing the respective functions. Additionally, a plurality of components illustrated in FIG. 1 may be integrated into one processor to realize the respective functions.

Figure 5:
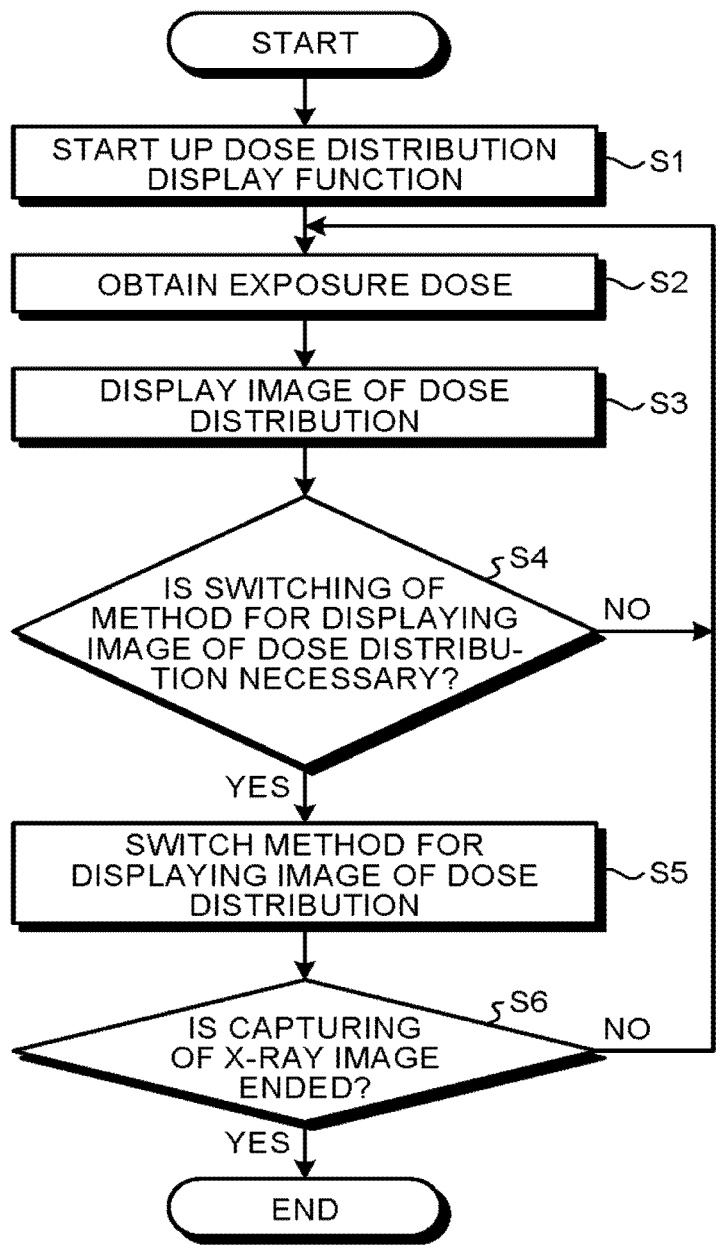
FIG. 5 is a diagram illustrating a flow of capturing an X-ray image from a start to an end according to the first embodiment.

Hereinafter, a flow of displaying the human body model 141 and the image of the dose distribution will be described. FIG. 5 depicts a flow of capturing an X-ray image from a start to an end.

First, after the capturing of the X-ray image is started, a function for displaying the image of the dose distribution is started up in S1. The function for displaying the image of the dose distribution may be manually started up by the operator through the operation unit 16, or alternatively, may be automatically started up by, for example, the system controller 17 when detecting the start of X-ray irradiation by the X-ray generator 11.

In S2, based on the X-ray irradiation condition or the geometric condition, the dose determination unit 20 obtains the exposure dose of the subject P. The obtained exposure dose is stored in the storage unit 18 so as to be readable by the system controller 17.

In S3, the image processor 15 reads information on the exposure dose from the storage unit 18 to generate an image of the dose distribution. The image processor 15 then superimposes the image of the dose distribution on the human body model 141 to generate a display image. The display unit 14 displays the display image in which the image of the dose distribution is superimposed on the human body model 141.

In S4, switching of the method for displaying the image of the dose distribution is determined. The switching of the method for displaying the image of the dose distribution here means making the visible range in the view direction on the surface of the human body model 141 transparent. Several types of timings for switching the method for displaying the image of the dose distribution can be set. Some examples will be described in the following.

Switching in Accordance with Exposure Dose

The display method is switched when the exposure dose in the invisible range in the view direction on the human body model 141 increases to a level requiring a caution. Specifically, the timing for switching is set for a case where a predetermined threshold for the exposure dose is exceeded or a case where the exposure dose reaches a range of a caution area defined in the vicinity of the threshold. A default value stored in the storage unit 18 in advance may be used as the threshold, or alternatively, a value determined by the operation unit 16 receiving the input from the operator may be used as the threshold.

Switching in Accordance with Irradiation Range

The display method is switched when the irradiation range on the human body model 141, which is obtained based on the opening degree of collimator blade (a position of the blade) or the geometric conditions for the supporter 13 and the table 19, includes part or all of a region on the human body model 141 where the dose is high. In order to determine whether the dose is high, a predetermined threshold stored in the storage unit 18 in advance may be used, or alternatively, a threshold determined by the operation unit 16 receiving the input from the operator may be used.

Switching in Accordance with Interruption of X-Ray Irradiation

Even while the X-ray image is being captured, there is a timing at which the X-ray irradiation is temporarily interrupted such that treatment operation is stopped. The display method is switched by the system controller 17 monitoring the interruption of the X-ray irradiation through the tube voltage and the tube electric current supplied to the X-ray tube of the X-ray generator 11. Alternatively, the display method may be switched when the operation unit 16 receives the input to stop the X-ray irradiation.

When the aforementioned timings are not applicable for the switching of the display method, the process returns to S2 and the exposure dose is obtained again.

In S5, the system controller 17 switches the method for displaying the image of the dose distribution on the display unit 14. The image processor 15 makes the visible range in the view direction on the surface of the human body model 141 transparent such that the dose distribution in the invisible range in the view direction can be observed in the view direction by being looked therethrough. The image of the dose distribution whose display method has been switched may be continuously displayed or returned to the original display after a predetermined period of time has elapsed. In addition, the dose distribution in the invisible range in the view direction may be hidden or displayed by being made transparent at a timing other than a timing that does not require the switching.

In S6, whether the capturing of the X-ray image is ended is determined. When the capturing of the X-ray image continues, the process returns to S2 and the exposure dose is obtained. When the capturing of the X-ray image is ended, the flow is terminated.

Figure 6:
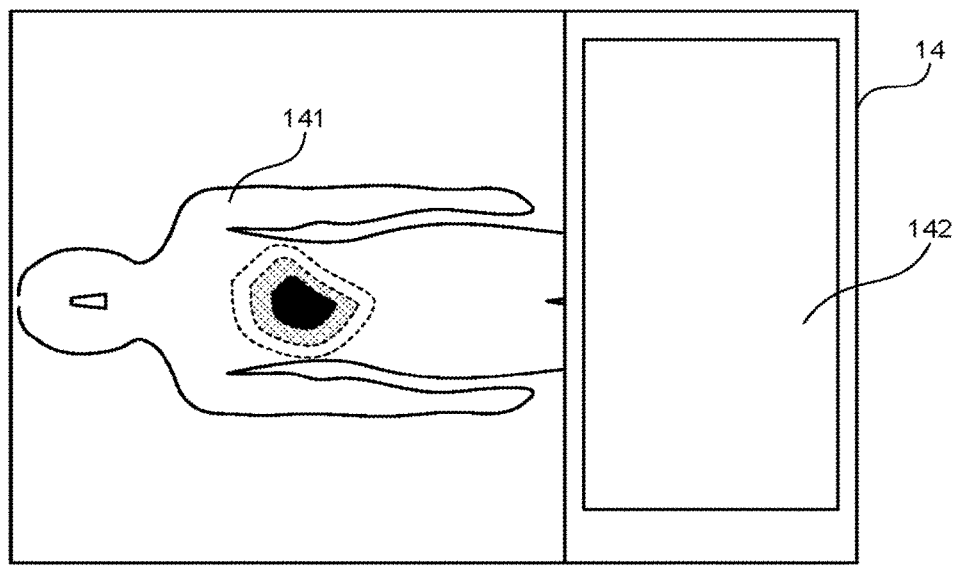
FIG. 6 is a diagram illustrating an example in which a view direction in the exemplary display illustrated in FIG. 3 is changed in accordance with a position of an operator.
Figure 7:
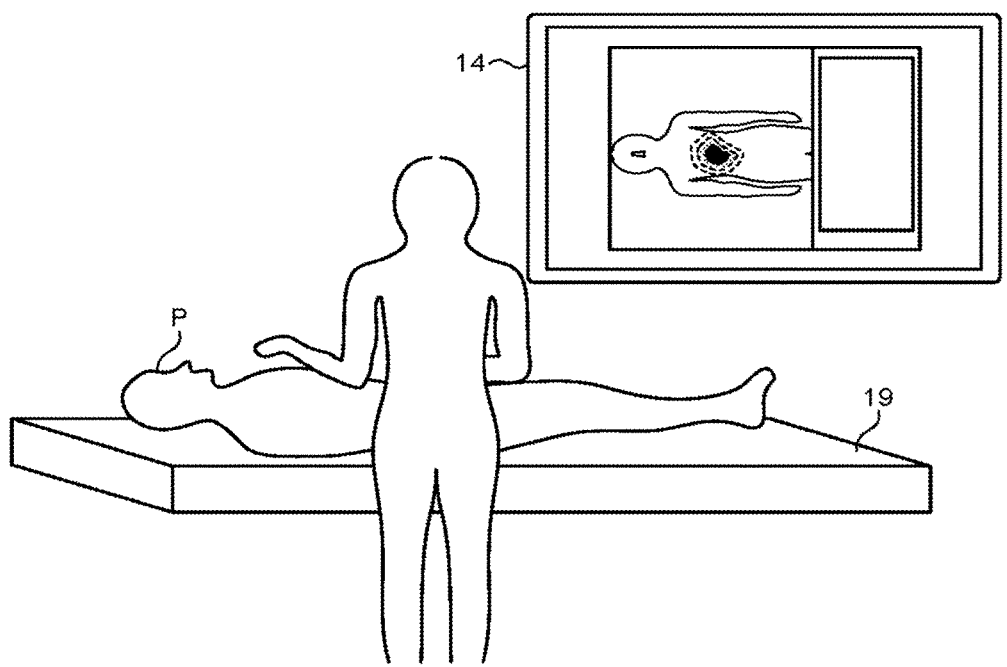
FIG. 7 is a diagram illustrating a positional relationship between the operator and the display unit relative to the subject when the exemplary display illustrated in FIG. 6 is displayed.

Meanwhile, the view direction of the human body model 141 displayed on the display unit 14 can be changed in accordance with a position of an operator. FIG. 6 depicts a state in which the human body model 141 facing the subject P, as illustrated in FIG. 3, is displayed on the display unit 14 in the view direction by being rotated counter clockwise by 90°. FIG. 7 depicts an exemplary position of the operator for which the human body model 141 illustrated in this FIG. 6 is displayed. The operator stands on the right side when observed from the subject P placed on his/her back on the table 19, whereas the display unit 14 is disposed on the left side of the subject P near the feet with a display surface facing to the side of the table 19. When the subject P is observed from the operator, the head is located on the left-hand side and the lower half of the body is located on the right-hand side. The view direction can be changed such that this condition is displayed as it is.

Figure 8:
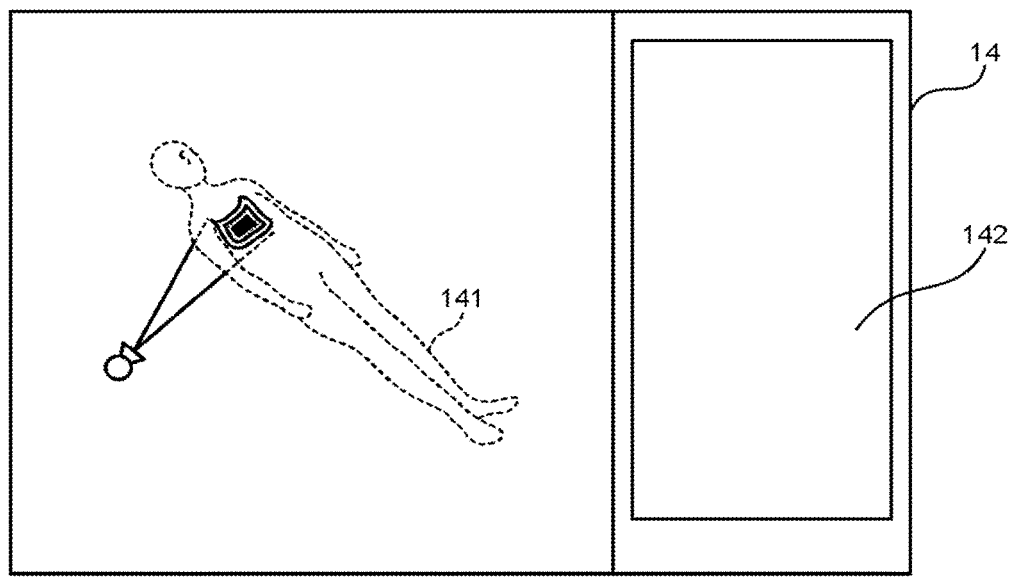
FIG. 8 is a diagram illustrating an example in which a view direction in the exemplary display illustrated in FIG. 3 is changed.

The view direction may be changed on the operation unit 16 or changed automatically in accordance with the position of the operator. In order to automatically change the view direction, for example, an infrared sensor is provided and a vicinity of a position at which approach is detected may be determined as the position of the operator. Alternatively, the position of the operator may be investigated through person detection on an image captured by a camera. The view direction in which the human body model 141 is displayed is not limited to a case where a body axis of the human body model is vertical or horizontal as illustrated in FIGS. 3 and 6, but may be determined to any direction. FIG. 8 depicts an example in which the view direction in the exemplary display illustrated in FIG. 3 is changed. For example, as illustrated in FIG. 8, the view direction in which the human body model 141 may be changed in accordance with input by an operator through the operation unit 16. Regarding the timing at which the view direction of the human body model 141 is switched, a position of the operator when the operator starts medical treatment may be first detected and that view may be continuously fixed. Alternatively, the view direction may be switched when the position of the operator is totally changed, for example, when the operator stands on an opposite side in a left-right direction when observed from the subject P. Additionally, the view direction may be accurately changed by thoroughly following a position where the operator is standing.

In the aforementioned first embodiment, the dose determination unit 20 obtains the exposure dose of the subject P and, based on this exposure dose, the image processor 15 generates an image of the dose distribution. Additionally, by making the human body model 141 representing the subject P transparent, the image processor 15 makes it possible to observe, by looking therethrough, the image of the dose distribution on the surface of the human body model 141, which image is not visible in the view direction serving as a current display direction of the human body model 141. As a result, the image of the dose distribution which is hidden and invisible in the view direction being displayed can be confirmed without changing a manner of observing the human body model 141 observed in the view direction being displayed. Thus, the positions of the X-ray generator 11 and the supporter 13 relative to the subject P are easily recognized, which makes it easy to determine the irradiation range of the X-ray. When the irradiation range of the X-ray can be easily determined, a period of time for which the subject P is exposed to radiation can be reduced and accordingly the exposure dose can be reduced.

Regarding the timing at which the image processor 15 makes the human body model 141 transparent, the image of the dose distribution on a rear side of the human body model 141 can be displayed depending on whether the display is required. As a result, the image of the dose distribution of the visible portion in the view direction can be carefully observed in usual times.

Additionally, the view direction in which the human body model 141 is displayed on the display unit 14 can be manually or automatically changed in accordance with the position of the operator obtained by the operation unit 16. As a result, the human body model 141 can be continuously confirmed in the view direction similar to a direction in which the operator observes the subject P and the positions of the X-ray generator 11 and the arm 131 of the supporter 13 can be easily recognized. Therefore, even when a position where the operator is standing is changed during medical treatment, it is easy to determine the irradiation range of the X-ray.

Second Embodiment

In an X-ray diagnostic apparatus 1 according to a second embodiment, a dose determination unit 20 obtains the exposure dose of a subject P and, based on this exposure dose, an image processor 15 generates an image of the dose distribution. Additionally, the image processor 15 generates a display image, in which the images of the dose distribution are superimposed, on a human body model 141 observed in a first view direction and the human body model 141 observed in a second view direction in which a body surface of the subject P on the rear side when observed in the first view direction is visible. A display unit 14 displays the display image in which the respective human body models 141 are arranged side by side. In the embodiment, the X-ray diagnostic apparatus is assumed to include one X-ray generator 11 and to be of a single-plane type in which one X-ray image can be captured at a time. In the second embodiment, the duplicated content with the first embodiment will be omitted. In addition, for the reference numerals in the drawings, common portions are given the similar reference numerals for the description thereof.

A flow of capturing the X-ray image from a start to an end is common with FIG. 5 described in the first embodiment. Hereinafter, the human body models 141 and the images of the dose distribution super imposed thereon, which are generated by the image processor 15 and displayed by the display unit 14, will be described.

Figure 9:
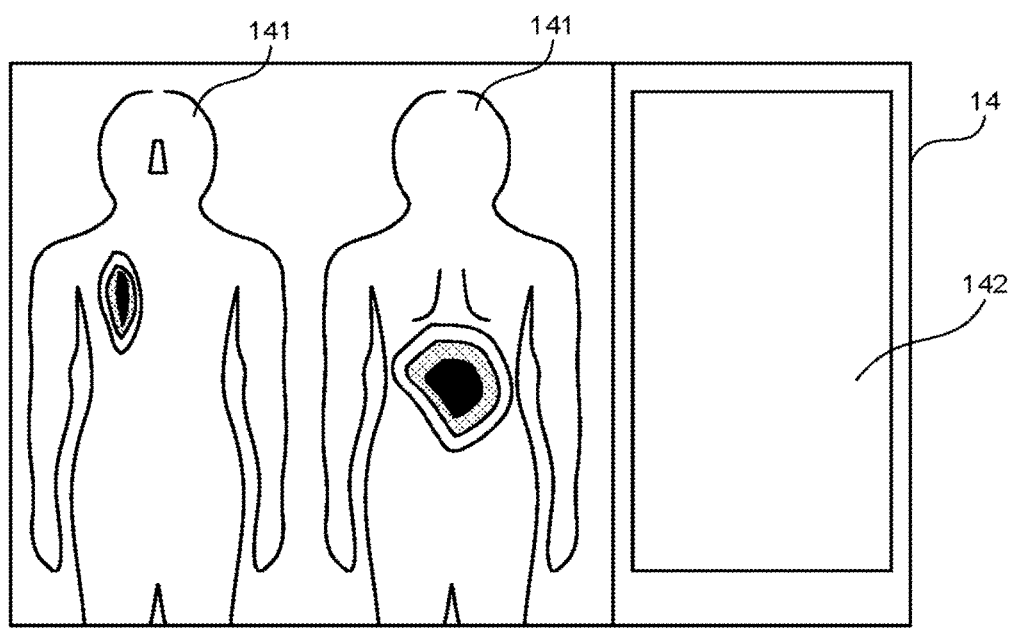
FIG. 9 is a diagram illustrating an example in which the human body models and the dose distributions are displayed on a display unit according to a second embodiment, when the subject is observed in the view direction and in a direction opposite thereto.

The image processor 15 superimposes the images of the dose distribution on the human body model 141 observed in the first view direction and the human body model 141 observed in the second view direction in which the body surface of the subject P on the rear side when observed in the first view direction is visible. FIG. 9 depicts the display unit 14 displaying a display image in which the images of the dose distribution are superimposed on the respective human body models 141, which are arranged side by side. An information display region 142 displays, as in FIGS. 3 and 6, buttons for operating, for example, the method for displaying the human body model 141 through an input device such as a mouse, information on the exposure dose in the irradiation range of the X-ray, an operation guide, a message indicating that a caution is required for the dose, and the like.

FIG. 9 depicts the display unit 14 displaying an image in which the human body model 141 whose ventral surface is visible is arranged on the left side and the human body model 141 whose back surface is visible is arranged on the right side. The image of the dose distribution is displayed on an upper right portion of the chest on the human body model 141 whose ventral surface is visible, whereas the image of the dose distribution is displayed around the waist on the human body model 141 whose back is visible. For example, when the positional relationship between the operator and the subject P is as in FIG. 7, the human body model 141 whose ventral surface is visible can be used to refer to the image of the dose distribution in a range visible from the operator and the human body model 141 whose back is visible can be used to refer to the image of the dose distribution in a range invisible from the operator.

Figure 10:
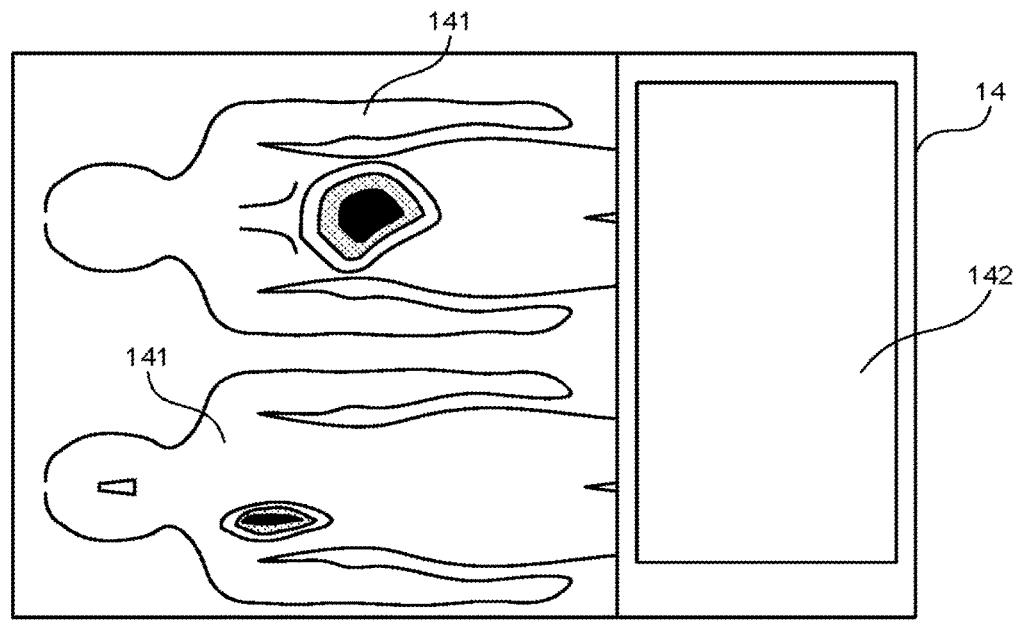
FIG. 10 is a diagram illustrating an example in which the view direction in the exemplary display illustrated in FIG. 9 is changed in accordance with a position of the operator.

The image processor 15 is capable of changing the view direction in accordance with the position of the operator. FIG. 10 depicts an exemplary image displayed by making a view direction to be displayed more in line with the positional relationship between the operator and the subject P in a situation where the head of the subject P is located on the left side and the feet thereof are located on the right side when observed from the operator. The human body model 141 displayed in the first view direction is displayed in a lower part to display an image in line with a condition of the subject P observed by the operator. Meanwhile, the human body model 141 observed in the second view direction is displayed in an upper part. In the second view direction, the body surface of the subject P on the rear side when observed in the first view direction is visible. The view direction in which the human body model 141 is displayed is not limited to a case where the body axis of the human body model 141 is vertical or horizontal as illustrated in FIGS. 9 and 10, but can be determined to any direction.

According to the aforementioned second embodiment, the image processor 15 generates a display image in which the image of the dose distribution is superimposed on each of the human body model 141 observed in one view direction and the human body model 141 observed from the rear side of the subject P when observed in the one view direction. The display unit 14 displays a display image in which the human body models 141 on which the images of the dose distribution generated by the image processor 15 are superimposed are arranged side by side.

As a result, the image of the dose distribution observed in one view direction can be confirmed, while the invisible dose distribution hidden by the subject P can be confirmed on another human body model at the same time. This makes it easy to determine the irradiation range of the X-ray.

Third Embodiment

In an X-ray diagnostic apparatus 1 according to a third embodiment, a dose determination unit 20 obtains the exposure dose of a subject P and, based on this exposure dose, an image processor 15 generates an image of the dose distribution. Additionally, the image processor 15 generates an image of a human body model 141 observed in a first view direction and also creates an image of the human body model 141 observed in a second view direction serving as the X-ray irradiation direction of an X-ray generator 11. The image processor 15 then generates a display image in which the images of the dose distribution are superimposed on the respective human body models 141 observed in the first and second view directions. A display unit 14 displays the respective human body models 141 arranged side by side. In the embodiment, the X-ray diagnostic apparatus is assumed to include one X-ray generator 11 and to be of the single-plane type in which one X-ray image can be captured at a time. In the third embodiment, the duplicated content with the first embodiment will be omitted. In addition, for the reference numerals in the drawings, common portions are given the similar reference numerals for the description thereof.

The image processor 15 generates a display image in which the images of the dose distribution are superimposed on the human body model 141 observed in the first view direction and the human body model 141 observed in the second view direction serving as the X-ray irradiation direction of the X-ray generator 11. In order to generate the image of the human body model 141 observed in the second view direction, the image processor 15 obtains the geometric condition for the supporter 13 or the X-ray generator 11. This geometric condition is as indicated as the geometric condition described in the first embodiment. The image processor 15 obtains the X-ray irradiation direction based on the geometric condition and generates an image of the human body model 141 in which this X-ray irradiation direction serves as the second view direction. The second view direction is changed based on a variation in the X-ray irradiation direction of the X-ray generator 11. The second view direction may be changed by precisely following the variation in the X-ray irradiation direction, or alternatively, may be changed at a predetermined interval.

Figure 11:
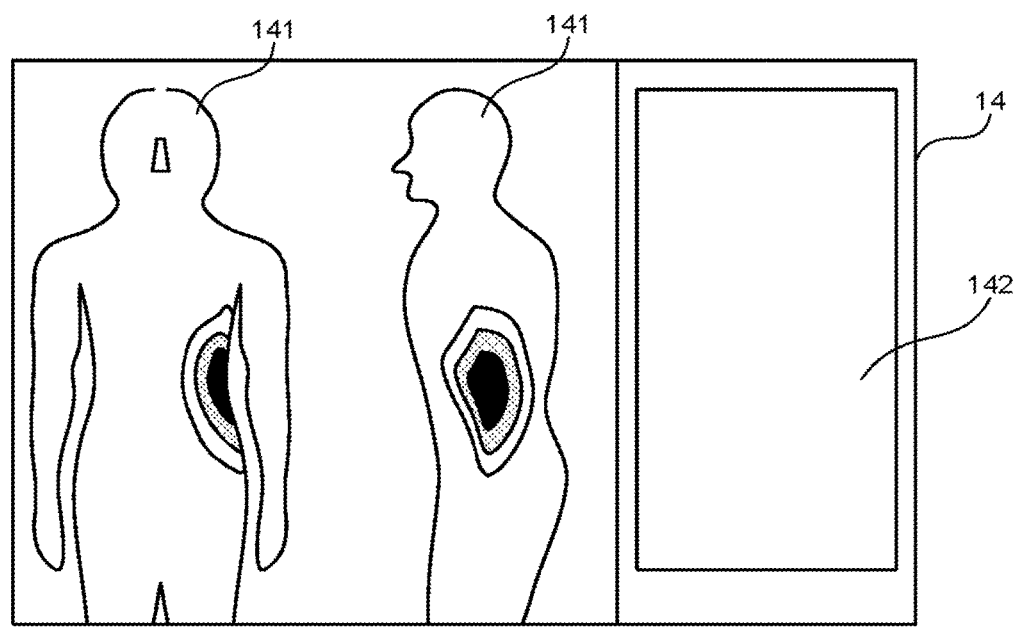
FIG. 11 is a diagram illustrating an example in which the human body models and the dose distributions are displayed on a display unit according to a third embodiment.

FIG. 11 depicts an exemplary image displayed by the display unit 14 in a case where the X-ray generator 11 irradiates, with the X-ray, an area around the waist on the left side of the body of the subject P. The display unit 14 arranges the human body model 141 whose ventral surface is visible on the left side and the human body model 141 whose left side of the body is visible on the right side to display. The human body model 141 whose ventral surface is visible is observed in the first view direction, whereas the human body model 141 whose left side of the body is visible is observed in the second view direction. The display unit 14 also displays the image of the dose distribution on an area around the waist on the left side of the body of each of the human body models 141. An information display region 142 displays, as in FIGS. 3 and 6, buttons for operating, for example, the method for displaying the human body model 141 through an input device such as a mouse, information on the exposure dose in the irradiation range of the X-ray, an operation guide, a message indicating that a caution is required for the dose, and the like.

According to the aforementioned third embodiment, the image processor 15 generates an image of the human body model 141 observed in the first view direction and an image of the human body model 141 observed in the second view direction serving as the X-ray irradiation direction of the X-ray generator 11. The image processor 15 also generates a display image in which the image of the dose distribution is superimposed on each of the human body models 141. The display unit 14 displays a display image in which the human body models 141 on which the images of the dose distribution generated by the image processor 15 are superimposed are arranged side by side.

As a result, even when the irradiation range of the X-ray is located at a position difficult to observe in one view direction, the image of the dose distribution in which the X-ray irradiation direction serves as the view direction can be confirmed on another human body model at the same time. This makes it easy to determine the irradiation range of the X-ray.

Fourth Embodiment

The aforementioned first to third embodiments have described a case where a display image is displayed by changing the method for displaying the human body model 141 such that the image of the dose distribution on the body surface on the rear side, which is hidden and invisible when observed in the first view direction, can be observed, or a case where a display image is displayed in which the images of the dose distribution are superimposed on the human body model 141 observed in the first view direction and the human body model 141 observed in the second view direction serving as the X-ray irradiation direction of the X-ray generator 11. A fourth embodiment will describe a case where a display image is displayed in which the image of the dose distribution on the body surface observed in the first view direction and the image of the dose distribution on the body surface on the rear side, which is hidden and invisible when observed in the first view direction, are superimposed on a single human body model.

In an X-ray diagnostic apparatus 1 according to the fourth embodiment, a dose determination unit 20 obtains the exposure dose of a subject P and, based on this exposure dose, an image processor 15 generates an image of the dose distribution. Additionally, the image processor 15 superimposes the image of the dose distribution on each of the body surface of a human body model 141 on a front side when observed in the first view direction and the body surface of the human body model 141 on the rear side when observed in the first view direction. Here, by making the human body model 141 transparent, the image processor 15 makes it possible to observe, by looking therethrough, the image of the dose distribution on the body surface of the human body model 141 on the rear side, which is not visible in the first view direction. A display unit 14 displays the human body model. In the fourth embodiment, the duplicated content with the first embodiment will be omitted. In addition, for the reference numerals in the drawings, common portions are given the similar reference numerals for the description thereof.

For example, based on the X-ray irradiation condition or the geometric conditions for the supporter 13 and the table 19, the dose determination unit 20 calculates the exposure dose on the whole body of the subject P including the body surface on the front side when observed in the first view direction and the body surface on the rear side when observed in the first view direction. The image processor 15 uses the exposure dose calculated by the dose determination unit 20 to generate an image of the dose distribution for each of radiation-exposed regions on the body surface of the subject P. The image processor 15 then superimposes, on the human body model 141, the image of the dose distribution on a region corresponding to the radiation-exposed region and generates a display image in which the human body model 141 is made transparent. The display unit 14 displays the generated display image. As a result, the X-ray diagnostic apparatus 1 according to the fourth embodiment can display, on a single human body model 141, the dose distribution on the body surface on the front side when observed in the first view direction and the dose distribution on the body surface on the rear side when observed in the first view direction.

Here, when the image of the dose distribution on the body surface on the front side when observed in the first view direction and the image of the dose distribution on the body surface on the rear side when observed in the first view direction are superimposed on a single human body model 141, the images of the dose distribution sometimes overlap in the view direction. In such a case, when the images of the dose distribution are displayed as they are, it can be difficult to distinguish the image of the dose distribution on the front side (image of the front-side dose distribution) from the image of the dose distribution on the rear side (image of the rear-side dose distribution). Accordingly, in a case where the image of the front-side dose distribution overlaps the image of the rear-side dose distribution in the view direction, the X-ray diagnostic apparatus 1 according to the fourth embodiment generates and displays a display image in which the respective images can be distinguished from each other.

Figure 12:
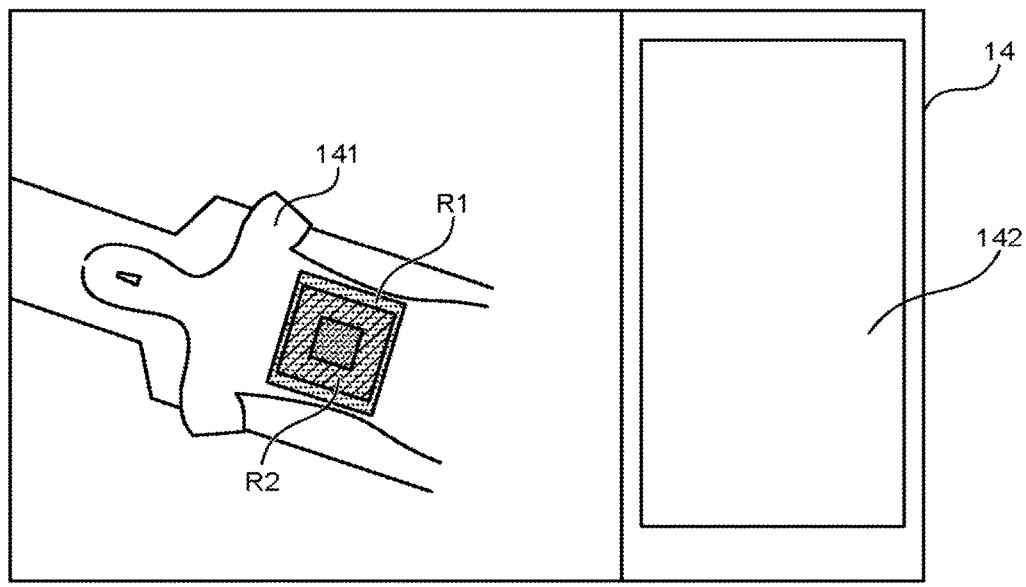
FIG. 12 is a diagram illustrating an example in which the human body model and the dose distributions are displayed on a display unit according to a fourth embodiment.

Specifically, when the image of the rear-side dose distribution, which is an image of the dose distribution on the body surface on the rear side when observed in the first view direction, and the image of the front-side dose distribution, which is an image of the dose distribution on the body surface on the front side when observed in the first view direction, overlap in the first view direction, the display unit 14 displays the image of the rear-side dose distribution and the image of the front-side dose distribution using different display methods. FIG. 12 depicts an example in which the human body model and the dose distribution are displayed on the display unit 14 according to the fourth embodiment. For example, as illustrated in FIG. 12, in a case where a region R1 of the image of the front-side dose distribution (a largest rectangular region in the drawing) overlaps, in the view direction, a region R2 of the image of the rear-side dose distribution (a rectangle within the region R1 in the drawing), the display unit 14 displays the region R1 and the region R2 using different display methods such that the respective regions can be distinguished from each other.

Here, the exposure dose is often expressed by different colors in the image of the dose distribution. Accordingly, as illustrated in FIG. 12, the display unit 14 displays the region R2 by, for example, adding a shade thereto to distinguishably display the region R2 overlapping the region R1. Specifically, in the X-ray diagnostic apparatus 1 according to the fourth embodiment, the image processor 15 determines whether the image of the front-side dose distribution overlaps the image of the rear-side dose distribution in the view direction. When the images are determined to overlap, the image processor 15 generates an image of the front-side dose distribution and an image of the rear-side dose distribution such that the respective images can be distinguished from each other. For example, the image processor 15 generates an image of the rear-side dose distribution to which a shade is added as illustrated in FIG. 12.

FIG. 12 has indicated an example in which a method for displaying the image of the rear-side dose distribution is changed. However, the embodiment is not limited thereto but a case where a method for displaying the image of the front-side dose distribution is changed may be employed. Alternatively, a case where both of methods for displaying the image of the front-side dose distribution and the image of the rear-side dose distribution are changed may be employed. Additionally, FIG. 12 has indicated an example in which a shade is added in order to distinguish the image of the front-side dose distribution from the image of the rear-side dose distribution. However, the embodiment is not limited thereto but the images may be displayed using any display method. For examples thereof, a case where an image of the dose distribution to which a netlike pattern is added is generated may be employed, or alternatively, a case where an image of the dose distribution obtained by emphasizing a boundary of an image located on an inner side among the images (for example, an outer boundary of the region R2 in FIG. 12) is generated may be employed.

Meanwhile, the method for displaying the image of the dose distribution can be changed at any timing. For example, a case where the display method is changed when the image of the front-side dose distribution overlaps the image of the rear-side dose distribution in accordance with change in the view direction may be employed. In this case, based on a positional relationship between the image of the front-side dose distribution and the image of the rear-side dose distribution on the human body model 141 and the view direction, the image processor 15 determines whether the image of the front-side dose distribution overlaps the image of the rear-side dose distribution in the view direction. When the images are determined to overlap, the image processor 15 generates an image of the dose distribution for changing the display method. Furthermore, a case where, in addition to a situation in which the image of the front-side dose distribution overlaps the image of the rear-side dose distribution in the view direction, the display method is changed when the images do not overlap may be employed, for example. In this case, the image processor 15 generates an image of the dose distribution for which the display method is changed for at least one of the image of the front-side dose distribution and the image of the rear-side dose distribution.

Meanwhile, the timing at which the image of the rear-side dose distribution is displayed can be set as necessary based on a predetermined condition. Specifically, as described in the first embodiment, the image of the rear-side dose distribution can be displayed based on a condition such as the exposure dose, the irradiation range, or interruption of the X-ray irradiation.

As described above, the X-ray diagnostic apparatus 1 according to the fourth embodiment displays the image of the front-side dose distribution and the image of the rear-side dose distribution on a single human body model 141 such that the respective images can be distinguished from each other. As a result, the X-ray diagnostic apparatus 1 makes it possible to confirm the dose distribution on the front side of the subject P and the dose distribution on the rear side thereof on a single human body model and to three-dimensionally recognize the positional relationships thereamong.

Fifth Embodiment

The aforementioned first to fourth embodiments have described a case where a display image in which the image of the dose distribution is superimposed on the human body model 141 is displayed. A fifth embodiment will describe a case where a display image indicating, in addition to a human body model 141, a three-dimensional model of a supporter 13 or a beam shape of radiated X-ray is displayed.

In an X-ray diagnostic apparatus 1 according to the fifth embodiment, a dose determination unit 20 obtains the exposure dose of a subject P and, based on this exposure dose, an image processor 15 generates an image of the dose distribution. Additionally, the image processor 15 superimposes the image of the dose distribution on the human body model 141. Here, by making the human body model 141 transparent, the image processor 15 makes it possible to observe, by looking therethrough, the image of the dose distribution on the body surface of the human body model 141 on the rear side, which is not visible in the first view direction. A display unit 14 displays the human body model. In the fifth embodiment, the duplicated content with the first embodiment will be omitted. In addition, for the reference numerals in the drawings, common portions are given the similar reference numerals for the description thereof.

Figure 13:
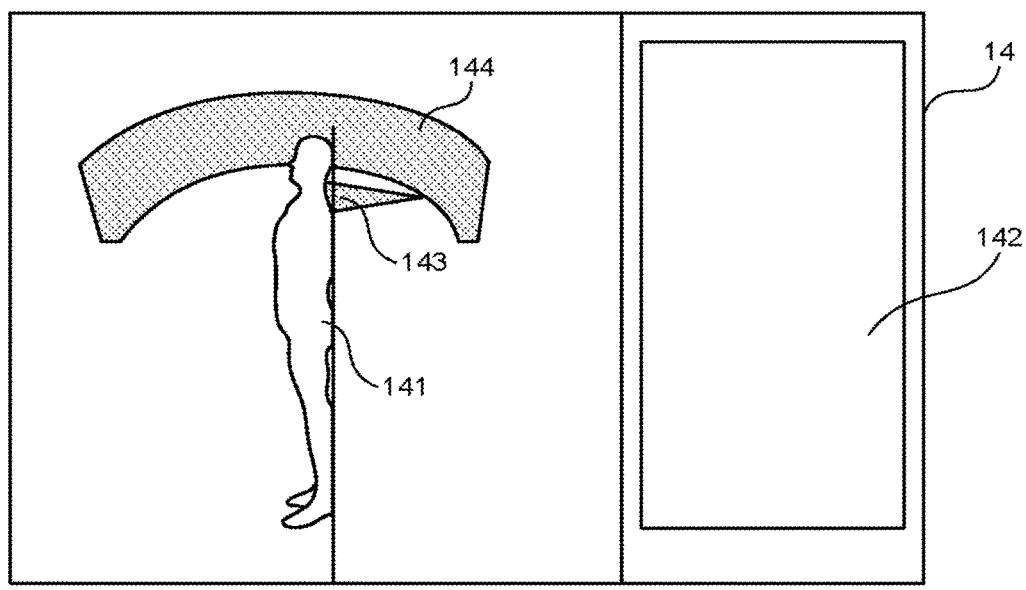
FIG. 13 is a diagram illustrating an example in which three-dimensional models are displayed on a display unit according to a fifth embodiment.

The image processor 15 according to the fifth embodiment generates an image including, in addition to a three-dimensional model representing the subject, at least one of a three-dimensional model representing the supporter 13 holding an X-ray generator 11 and a three-dimensional model representing a beam shape of the X-ray with which the subject is irradiated. For example, based on the X-ray irradiation condition or the geometric conditions for the supporter 13 and the table 19, the image processor 15 calculates a position of the irradiation range of the X-ray relative to the subject P or a position of the supporter 13 relative to the subject P. The image processor 15 then generates a display image in which the three-dimensional model representing the beam shape of the X-ray or the three-dimensional model representing the supporter 13 is indicated at a position corresponding to the calculated position in three-dimensional space including the human body model 141. FIG. 13 is a diagram illustrating an example in which three-dimensional models are displayed on the display unit according to the fifth embodiment.

For example, as illustrated in FIG. 13, the image processor 15 generates a display image indicating, in addition to the human body model 141, a beam shape model 143 representing the beam shape of the X-ray and an arm model 144 representing the arm 131. Here, a positional relationship of the beam shape model 143 relative to the human body model 141 varies depending on change in the position of the X-ray generator 11 caused by driving of the supporter 13. Specifically, the image processor 15 regularly obtains positional information on the X-ray generator 11 relative to the subject P and generates a display image in which the position of the beam shape model 143 is changed in accordance with the obtained positional information. A shape of the beam shape model 143 also varies depending on change in the opening degree of collimator blade. Specifically, the image processor 15 regularly obtains information on the opening degree of collimator blade and generates a display image in which the shape of the beam shape model 143 is changed in accordance with the obtained opening degree of collimator blade.

Meanwhile, a positional relationship of the arm model 144 relative to the human body model 141 varies depending on change in the position of the arm 131 caused by driving of the supporter 13. Specifically, the image processor 15 regularly obtains positional information on the arm 131 relative to the subject P and generates a display image in which the position of the arm model 144 is changed in accordance with the obtained positional information.

The display unit 14 updates the display image every time the display image is generated by the image processor 15. As a result, the display image is changed by following driving of the supporter 13 and change in the opening degree of collimator blade.

As described above, the X-ray diagnostic apparatus 1 according to the fifth embodiment displays a display image indicating, in addition to the human body model 141, the three-dimensional model of the supporter 13 or the beam shape of radiated X-ray. As a result, the X-ray diagnostic apparatus 1 makes it possible to quickly confirm an irradiation position and the irradiation range of the X-ray on the subject P. The X-ray diagnostic apparatus 1 also makes it possible to quickly confirm the positional relationship between the subject P and the supporter 13.

The aforementioned first to fifth embodiments have described an example in which, by making the human body model 141 transparent, an invisible portion hidden on the surface of the human body model is made visible therethrough. However, the embodiments are not limited thereto. For example, a case where the human body model 141 has a mesh shape may be employed. In this case, the image processor 15 generates a human body model 141 whose surface has a mesh shape. Specifically, the image processor 15 generates a display image in which the shape of the human body model 141 can be recognized by making the surface of the human body model 141 mesh-shaped, while the image of the dose distribution on the body surface on the rear side when observed in the first view direction can be monitored through intervals of the mesh.

In the X-ray diagnostic apparatus according to at least one of the embodiments described above, the image processor 15 generates an image of the human body model 141 in a display direction and an image of the dose distribution which is impossible or difficult to observe in that display direction, and the display unit 14 simultaneously displays these images. The displayed image is in line with an actual condition of the subject observed by the operator and thus the operator easily recognizes the position of the X-ray generator, the arm, or the like relative to the subject. This makes it easy to determine the irradiation range of the X-ray.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus, comprising:
an X-ray generator configured to radiate an X-ray;
processing circuitry configured to obtain an exposure dose of a subject due to the X-ray radiated from the X-ray generator and to generate an image in which a dose distribution based on the exposure dose is superimposed on a three-dimensional model representing the subject; and
a display configured to display the image,
wherein the processing circuitry is further configured to generate the image, in which the dose distribution on a body surface on a rear side when observed in a first view direction is visible, the image showing the three-dimensional model observed in the first view direction.

2. The X-ray diagnostic apparatus according to claim 1, wherein the processing circuitry is further configured to generate the image, in which the three-dimensional model is made semitransparent or mesh-shaped.

3. The X-ray diagnostic apparatus according to claim 1, wherein the dose distribution obtained by the processing circuitry is an accumulated skin exposure dose based on the X-ray sequentially radiated onto the subject.

4. The X-ray diagnostic apparatus according to claim 1, wherein the display changes a method for displaying the three-dimensional model based on a predetermined condition and displays the image in which the dose distribution on the body surface on the rear side when observed in the first view direction is visible.

5. The X-ray diagnostic apparatus according to claim 4, wherein the display changes the method for displaying the three-dimensional model based on an angle or a position of a supporter holding the X-ray generator.

6. The X-ray diagnostic apparatus according to claim 4, wherein the display changes the method for displaying the three-dimensional model when the exposure dose of the subject in a range irradiated with the X-ray exceeds a predetermined threshold.

7. The X-ray diagnostic apparatus according to claim 4, wherein the display changes the method for displaying the three-dimensional model when the X-ray generator stops X-ray irradiation.

8. The X-ray diagnostic apparatus according to claim 1, wherein the first view direction is a direction in which a front surface of a body of the subject is displayed.

9. The X-ray diagnostic apparatus according to claim 1, wherein the three-dimensional model is a human body model.

10. The X-ray diagnostic apparatus according to claim 1, wherein, when a rear-side dose distribution, which is the dose distribution on the body surface on the rear side when observed in the first view direction, and a front-side dose distribution, which is the dose distribution on the body surface on a front side when observed in the first view direction, overlap in the first view direction, the display displays the rear-side dose distribution and the front-side dose distribution using different display methods.

11. The X-ray diagnostic apparatus according to claim 1, wherein the processing circuitry is further configured to generate the image including, in addition to the three-dimensional model representing the subject, at least one of a three-dimensional model representing a supporter holding the X-ray generator and a three-dimensional model representing a beam shape of the X-ray radiated onto the subject.

12. An X-ray diagnostic apparatus of a single-plane type having only one X-ray generator, comprising:
processing circuitry configured to obtain an exposure dose of a subject due to an X-ray radiated from the X-ray generator and to generate an image in which a dose distribution based on the exposure dose is superimposed on a three-dimensional model representing the subject; and
a display configured to display the image, wherein
the processing circuitry is further configured to generate a display image in which the three-dimensional model observed in a first view direction serving as a direction in which the three-dimensional model is displayed on the display and the three-dimensional model observed in a second view direction in which a body surface on a rear side when observed in the first view direction is visible are arranged.

13. The X-ray diagnostic apparatus according to claim 12, wherein the second view direction is a direction in which the X-ray generator radiates the X-ray.

\* \* \* \* \*